United States Patent [19]

Haber et al.

[11] Patent Number: 5,112,307
[45] Date of Patent: May 12, 1992

[54] DENTAL SYRINGE HAVING A MEDICATION FILLED CARPULE AND AN AUTOMATICALLY-DETACHING PISTON STEM

[75] Inventors: Terry M. Haber, Lake Forest; Clark B. Foster, Laguna Niguel, both of Calif.

[73] Assignee: Habley Medical Technology Corp., Laguna Hills, Calif.

[21] Appl. No.: 513,246

[22] Filed: Apr. 24, 1990

[51] Int. Cl.$^5$ ............................................... A61M 5/00
[52] U.S. Cl. .................................. 604/110; 604/220; 604/228; 604/232; 604/240; 604/197
[58] Field of Search ............... 604/110, 197, 198, 187, 604/218, 220, 228, 232, 234, 235, 240–241, 263; 433/89, 90

[56] References Cited

U.S. PATENT DOCUMENTS

| | | | |
|---|---|---|---|
| 4,738,663 | 4/1988 | Bogan | 604/198 |
| 4,747,830 | 5/1988 | Gloyer et al. | 604/110 |
| 4,767,413 | 8/1988 | Haber et al. | 604/198 |
| 4,790,822 | 12/1988 | Haining | 604/110 |
| 4,808,169 | 2/1989 | Haber et al. | 604/110 |
| 4,813,426 | 3/1989 | Haber et al. | 128/763 |
| 4,820,275 | 4/1989 | Haber et al. | 604/232 |
| 4,834,717 | 5/1989 | Haber et al. | 604/193 |
| 4,850,374 | 7/1989 | Diaz-Ramos | 128/763 |
| 4,863,427 | 9/1989 | Cocchi | 604/228 |
| 4,892,107 | 1/1990 | Haber | 128/763 |
| 4,909,794 | 3/1990 | Haber et al. | 604/110 |
| 4,915,701 | 4/1990 | Halkyard | 604/241 |
| 4,919,657 | 4/1990 | Haber et al. | 604/232 |
| 4,923,443 | 5/1990 | Greenwood et al. | 604/110 |
| 4,931,040 | 6/1990 | Haber et al. | 604/110 |
| 4,950,240 | 8/1990 | Greenwood et al. | 604/228 |

Primary Examiner—Stephen C. Pellegrino
Assistant Examiner—Michael Rafa
Attorney, Agent, or Firm—Townsend and Townsend

[57] ABSTRACT

A reusable dental syringe including a conventional medication filled carpule and a conventional double-ended needle cannula which is to be retracted into a compact enclosure to permit the safe handling and disposal of the cannula while avoiding an accidental needle stick and the possible spread of disease. The carpule is inserted into a hollow carpule adapter to engage a movable needle carrier at the distal end of the adapter. The combination carpule and adapter are loaded into the cylinder of the syringe, and the needle cannula is attached to the needle carrier to penetrate the carpule. At the conclusion of an injection, the combination carpule and carpule adapter are rotated outwardly from the syringe cylinder, and the carpule is then pulled rearwardly through the adapter, whereby to correspondingly relocate and anchor the movable needle carrier at the proximal end of the adapter. Accordingly, the needle cannula is retracted into and surrounded by the adapter so as to be irretrievably located and rendered non-reusable therewithin.

20 Claims, 7 Drawing Sheets

FIG. 16

DENTAL SYRINGE HAVING A MEDICATION FILLED CARPULE AND AN AUTOMATICALLY-DETACHING PISTON STEM

BACKGROUND OF THE INVENTION

1. Field of the Invention

This invention relates to a reusable, carpule based dental syringe having a double-ended cannula which is to be retracted within a compact enclosure to permit the safe handling and disposal of the cannula while avoiding an accidental and possibly life-threatening needle stick.

2. Background Art

Dental syringes of the type having a pre-filled carpule of fluid medication and a double-ended hypodermic needle cannula are well known in the art for injecting such medication from the carpule to a targeted tissue area of a patient. However, at the completion of the injection, the needle cannula is typically locked in an axially extended position projecting outwardly from a distal bore formed through the syringe cylinder.

In some cases, the syringe may be used to treat a patient having a communicable disease. Prior to disposing the syringe, the needle cannula is frequently broken or destroyed to prevent reuse. Dental office workers are especially susceptible to accidental and potentially infectious needle sticks due to the careless handling or breaking of the needle and disposing of the syringe after use. The resulting mini-accident caused by an accidental needle stick typically requires a blood test for such diseases as AIDs and hepatitis. The corresponding cost and inefficiency of testing dental office workers who have received such an accidental needle stick result in considerable waste, which may be particularly damaging to a dental facility which is striving for economy.

The following U.S. patent and applications, which have been or will be assigned to the assignee of the present invention, disclose carpule based dental syringes having a retractable needle cannula and a flexible locking arm for controlling the movement of said carpule relative to the cylinder of the syringe: U.S. Pat. No. 4,767,413 issued Aug. 30, 1988; U.S. patent application Ser. No. 135,607 filed Dec. 21, 1987; and U.S. patent application Ser. No. 270,094, filed Nov. 14, 1988.

SUMMARY OF THE INVENTION

In general terms, a reusable dental syringe is disclosed including a hollow cylinder having open proximal and distal ends and an axially aligned hollow body portion. A conventional medication filled carpule is pushed through a hollow carpule sleeve for receipt by a movable needle carrier at the distal end of the sleeve, and the combination carpule and sleeve are loaded into the cylinder through a longitudinally extending opening therein. A conventional hub supported, double-ended needle cannula is attached to the needle carrier via the open distal end of the cylinder so as to penetrate the carpule and communicate with the interior thereof. A hollow control rod is advanced distally, against the bias of a helical compression spring, through the hollow body of the syringe and the open proximal end of the syringe cylinder so that a retaining sleeve at one end of the control rod will be correspondingly advanced into surrounding engagement with the proximal end of the carpule to prevent displacement of the carpule relative to the cylinder. A flexible spring arm, which carries a release button at one end thereof, is attached to and movable with the control rod until the release button pops through a hole in the syringe body to lock the control rod at its distally advanced position. A plunger stem is slidable distally through the hollow control rod to be connected to and control the movement of a piston through the carpule so that medication may be expulsed from the carpule via the needle cannula.

In operation, the dentist locates the needle cannula at a targeted tissue area of the patient and slides the stem distally through the hollow control rod and into the carpule. The tip of the stem dilates a frangible insert disposed within the proximal end of the piston and is retained in engagement, therewith for joint movement of the tip of the stem and piston until the frangible insert is broken, as described below. The distal movement of the stem drives the piston through the carpule to administer an injection of the medication into the targeted tissue. Upon completing the injection, and while holding the carpule against axial displacement, the dentist presses the release button of the spring arm through the hole in the syringe body to release the control rod from its distally advanced position, whereby the formerly compressed spring is now free to return to the relaxed condition. The control rod and stem are then withdrawn rearwardly through the syringe body and away from the carpule, such that the retaining sleeve of the control rod is moved out of engagement with the carpule and the stem is disconnected from the piston. A sliding collar surrounding the piston stem abuts a shoulder formed in the body portion of the syringe. The collar forms a support for the piston tip upon retraction of the head. As the tip of the stem is fully withdrawn from the plunger, the insert breaks, thereby disengaging the tip from the retainer and preventing refilling or reuse of the carpule.

The combination carpule and sleeve are rotated downwardly, around an enlarged end of the body portion, through the longitudinally extending opening in the syringe cylinder. Next, the dentist grasps and pulls the carpule rearwardly through the sleeve to correspondingly relocate the movable needle carrier and the needle cannula attached thereto towards the proximal end of the sleeve. The needle carrier is anchored in its relatively proximal position by means of locking detents located at the proximal end of the sleeve to prevent any further displacement of the needle cannula. Accordingly, the needle cannula is retracted into and surrounded by the sleeve to form a safe and compact package which is suitable for disposal and in which the cannula is rendered irretrievable and non-reusable to thereby avoid an accidental needle stick and the possible spread of disease.

BRIEF DESCRIPTION OF THE DRAWINGS

FIG. 5' is a cross-section taken along lines 5'—5' of FIG. 5;

DESCRIPTION OF THE PREFERRED EMBODIMENT

Figure 1:
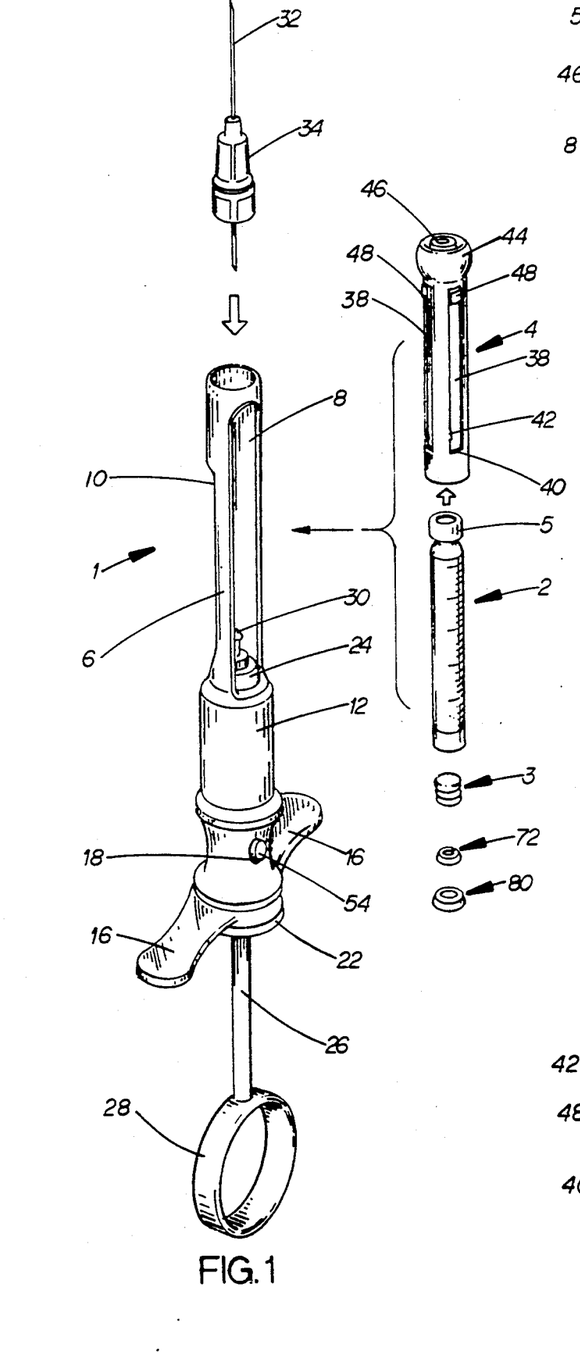
FIG. 1 shows a partially exploded view of the dental syringe which forms the present invention.

The carpule based, reusable dental syringe 1 of the present invention is now described in detail while referring to the drawings, where FIG. 1 shows a partially exploded view of the syringe 1 and a combination carpule 2 and sleeve 4. Carpule 2, which is typically formed from glass or other transparent material is of conventional design and includes a elastomeric piston 3 located at the proximal end thereof. Piston 3 includes a frangible insert 72 which is installed within the piston prior to insertion into carpule 2. Carpule 2 is filled with a supply of fluid medication, such as novocaine, or the like. The details of sleeve 4 will be described when referring to FIGS. 2 and 3.

Figures 4, 4A, 5:
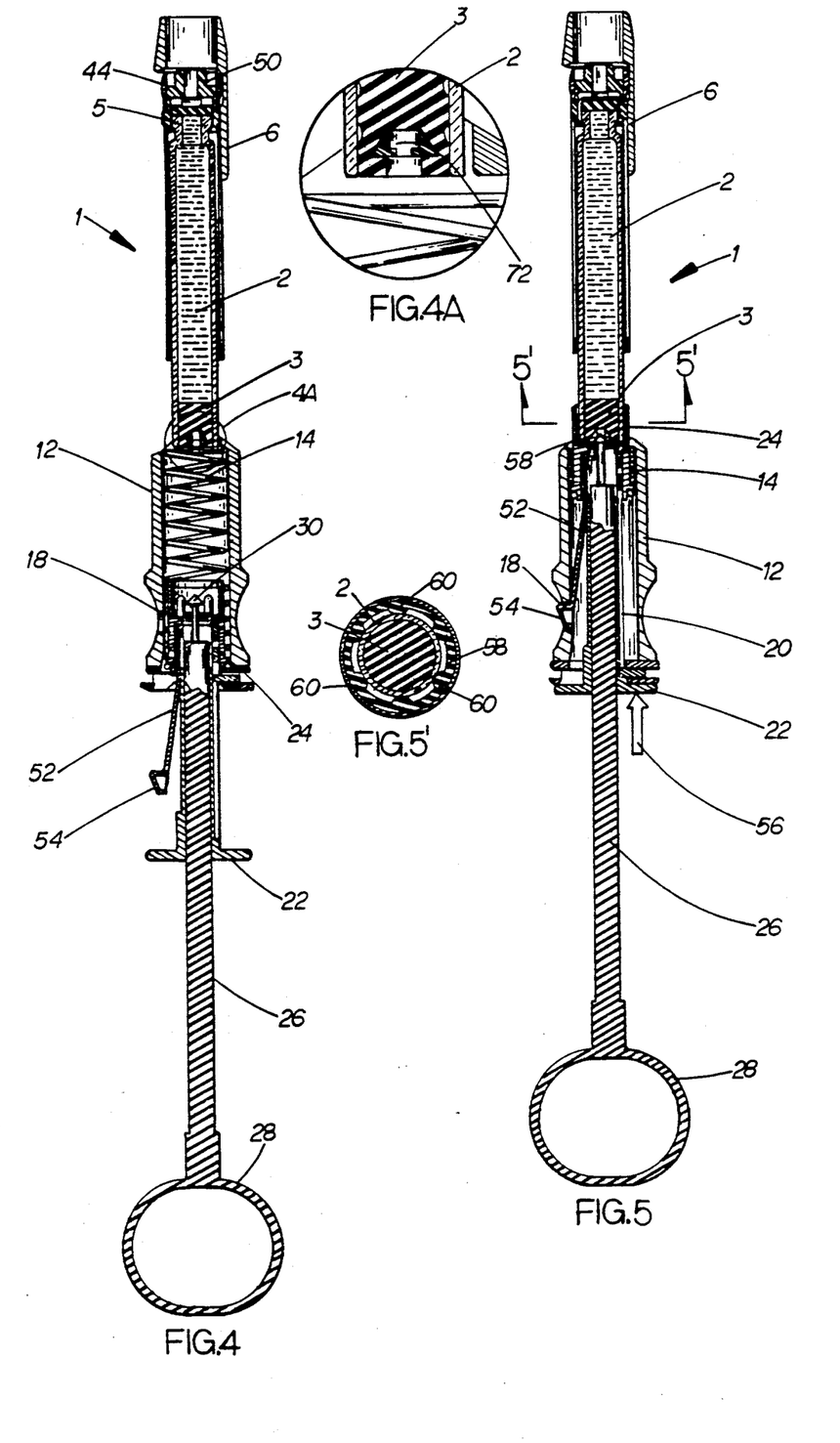
FIG. 4 is a cross-section of the dental syringe in a pre-injection state.
FIG. 4a is an enlarged view of section 4a of FIG. 4.
FIGS. 5-7 are cross-sections of the dental syringe in an injection state where medication is expulsed from the carpule to a targeted tissue area via a conventional double-ended needle cannula.

The syringe 1 includes a hollow cylinder or barrel 6 having open proximal and distal ends, a longitudinally extending opening 8 formed through one side of the cylinder (for removable receipt of the combination carpule 2 and sleeve 4), and a longitudinally extending window 10 formed through the opposite side (for gaining visible access to the medication filled carpule when such carpule is loaded into the interior of hollow cylinder 6). Coextensively joined to and axially aligned with the cylinder 6 is a hollow body portion 12. Located within the body portion 12 of syringe 1 is a helical compression spring 14, as seen in FIG. 4. Projecting radially outward in opposite directions from the body portion 12 is a pair of finger ledges 16. A hole 18 (best illustrated in FIG. 4) is formed through one side of body portion 12 between the oppositely extending finger ledges 16. The purpose of hole 18 for receiving a spring biased button 54 therethrough will be described later when referring to FIG. 4.

A hollow control rod 20 (as seen in FIG. 4) is slidably received in and adapted for axial and reciprocal movement through the hollow body portion 12 of syringe 1. Affixed to one end of the control rod 20 is a disk-like arming flange 22. Affixed to the opposite end of control rod 20 is a hollow retaining sleeve 24 having a shoulder 25. (See FIG. 9A.) As will soon explained, a force for moving the control rod 20 distally through hollow body portion 12 is applied to the arming flange 22, whereby to correspondingly advance retaining sleeve 24 (against the bias of compression spring 14) through the open proximal end of cylinder 6 for surrounding and engaging the proximal end of carpule 2. A flexible spring arm 52 (as seen in FIG. 4) is attached to and movable with the control rod 20 to releasably lock the control rod in a relatively distal position with the retaining sleeve 24 thereof securely engaging the carpule 2 for a purpose that will soon be described.

Figures 9, 9A, 10, 11, 12:
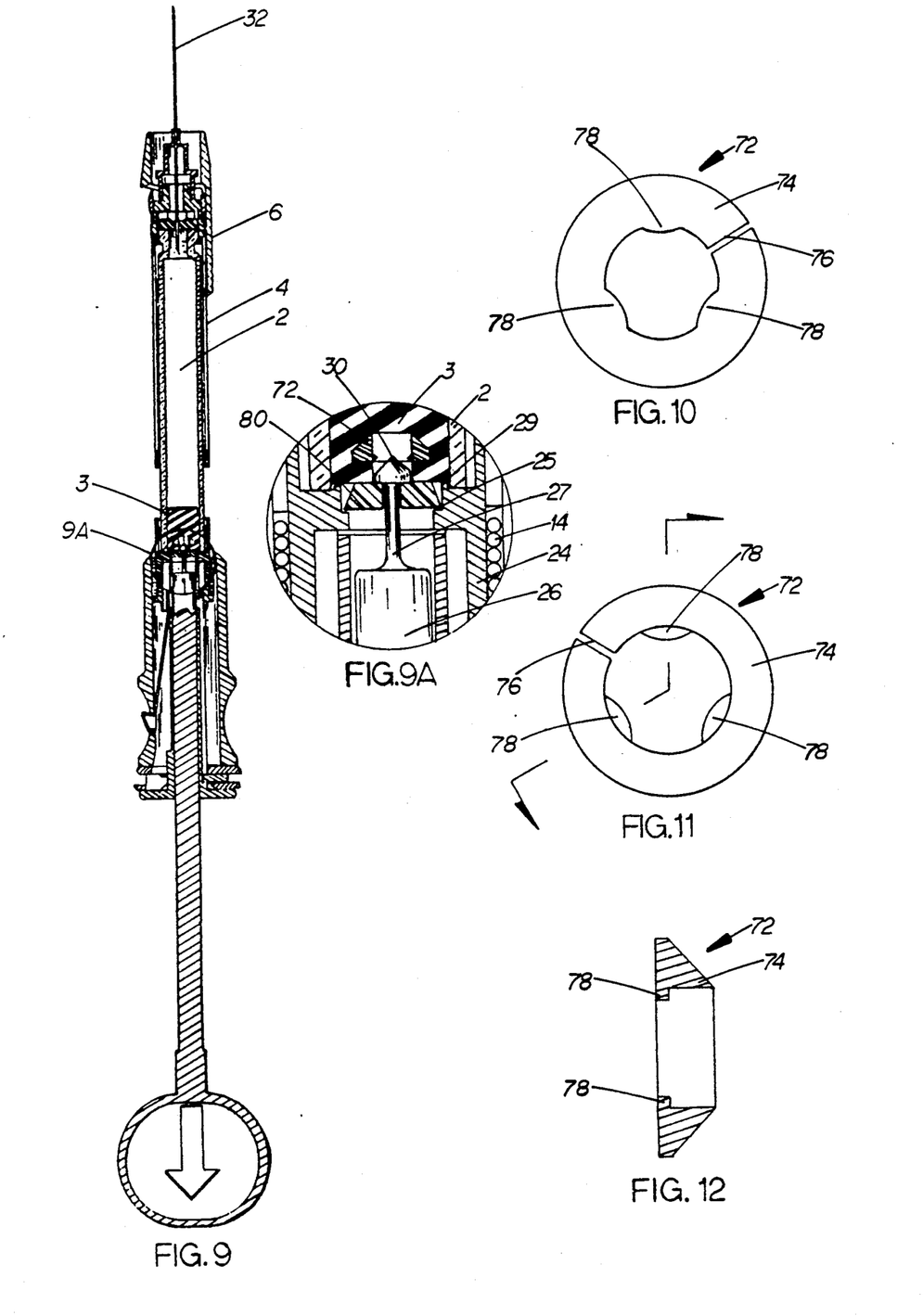
FIG. 9 is a cross-section of the dental syringe in a post-injection state.
FIG. 9a is an enlarged view of section 9a of FIG. 9 shown after the carpule is rendered nonreusable by breaking of an insert member.
FIG. 10 is a bottom plan view of the insert.
FIG. 11 is a top plan view of the insert.
FIG. 12 is a cross-section taken along lines 12—12 of FIG. 11.

A plunger stem 26 is slidably received in and adapted for axial and reciprocal movement through the hollow control rod 20, such that stem 26 is coaxially aligned with each of the body portion 12, compression spring 14 and control rod 20. (See FIG. 4.) Affixed to one end of stem 26 is a thumb ring 28, and affixed to the opposite end of stem 26 is a conically-shaped tapered tip 30. Opposite the conically-shaped tapered surface, and shown best in FIG. 9A, is a flat proximal surface 29. A reduced-diameter stem 27 is formed between stem 26 and tip 30. As will soon be explained, the movement of stem 26 in a distal direction through hollow control rod 20 is manually controlled at the thumb ring 28, whereby to correspondingly advance piston head 30 for connection of the piston head to the plunger 3 of carpule 2 so that said plunger can be driven through the carpule for expulsing the fluid medication therefrom. A sliding collar 80 surrounds reduced-diameter stem 27 for engagement with shoulder 25 of retaining sleeve 24.

A frangible insert 72 is positioned within the proximal end of piston 3. Referring to FIGS. 10-12, frangible insert 72 includes a circular insert ring 74 having a radial gap 76 formed between the inner and outer peripheries of the insert ring so as to permit dilation thereof, to be described below. Three frangible ears 78 are spaced equidistant about the inner periphery of insert ring 74 at its proximal end. Ears 78 engage tip 30 for joint movement of the tip and insert.

Syringe 1 is associated with a conventional double-ended hypodermic needle cannula 32. Cannula 32 is affixed to a screw threaded needle hub 34 and is adapted to communicate with the carpule 2 at the interior of cylinder 6 by way of the sleeve 4. That is to say, in the assembled relationship as seen in FIG. 4, needle hub 34 is connected to sleeve 4 via the open distal end of cylinder 6, such that one end of cannula 32 projects inwardly into the cylinder 6 to penetrate the carpule 2, and the opposite end of cannula 32 projects outwardly from the cylinder 6 to deliver the medication during the administration of an injection.

Figure 2:
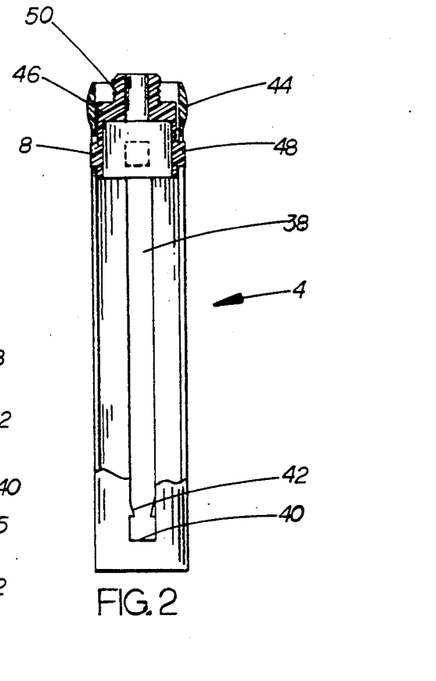
FIGS. 2 and 3 show partial cross-sections of a sleeve which is to be interfaced with a conventional medication filled carpule and loaded into the cylinder of the dental syringe of FIG. 1.
Figure 3:
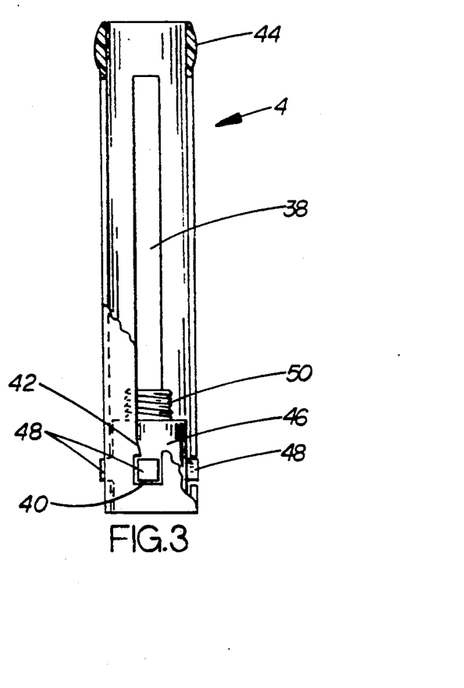

More particularly, and referring concurrently to FIGS. 1-3 of the drawings, the sleeve 4 includes a hollow, open ended tube-like body having a diameter which is sized to receive the medication carpule 2 therewithin. A plurality of evenly spaced, longitudinally extending tracks 38 are formed through the body of sleeve 4. Located at the rearward or proximal end of each track 38 and spaced axially from one another is a stop 40 and a locking detent 42. The purpose of stops 40 and locking detents 42 will soon be described. The forward or distal end of sleeve 4 includes a head portion 44 having a slightly enlarged diameter relative to the tube-like body for the dual purpose of creating a reliable snap fit of the sleeve 4 within the syringe cylinder 6 while also establishing a pivot surface for permitting sleeve 4 to rotate outwardly from the cylinder to achieve an important advantage that will be disclosed hereinafter when referring to FIG. 14.

A needle carrier 46 is located in and movable through the hollow interior of sleeve 4. Needle carrier 46 includes a generally hollow body and a plurality of radially projecting latches 48 which are received within and slidable through respective tracks 38 of sleeve 4. As shown in FIG. 2, the needle carrier 46 is initially positioned forwardly in the sleeve 4 and at the distal end thereof so that when the carpule 2 is inserted into the sleeve, end cap 5 of the carpule will be received by and attached to the needle carrier. The needle carrier 46 also includes a screw threaded bore 50 which, after carpule 2 has been inserted into sleeve 4 and the combination carpule and sleeve have been loaded into the syringe cylinder 6 through opening 8, is adapted to be mated to the screw threaded hub 34 via the open distal end of cylinder 6. Thus, the inwardly projecting end of needle cannula 32 will extend through the bore 50 of needle carrier 46 to penetrate the carpule 2 at the interior of sleeve 4, best shown in FIG. 6.

As shown in FIG. 3, when the needle carrier 46 slides rearwardly towards the proximal end of sleeve 4, the latches 48 ride through tracks 38 until such latches are received in the spaces between stops 40 and locking detents 42. The latches 48 are thereby permanently retained between stops 40 and detents 42 to block any further displacement of needle carrier 46 through sleeve 4 and thereby anchor said needle carrier at the proximal end of the sleeve, the advantage of which will be described when referring to FIGS. 15 and 16.

Referring now to FIG. 4 of the drawings, the dental syringe 1 is shown in the pre-injection state after the carpule has been inserted into and pushed forwardly through the sleeve 4 and the combination carpule and sleeve have been loaded into the syringe cylinder 6, such that the relatively large head 44 of sleeve 4 is detachably snap-fit within the cylinder. As previously indicated, the needle carrier 46 is initially positioned at the distal end of sleeve 4 to receive end cap 5 of the carpule 2 below the bore 50.

As was also earlier indicated, a flexible spring arm 52 is connected at one end of control rod 20 and movable therewith. Projecting radially from the proximal end of spring arm 52 is a release button 54 which is aligned and sized for receipt within a hole 18 through the body portion 12 of syringe 1 (best illustrated in FIG. 5) for the purpose of locking control rod 20 in a relatively distal position relative to said body portion. However, in the pre-injection state of FIG. 4, the control rod 20 is in a proximal position relative to body portion 12, and the compression spring 14 which surrounds the control rod within body portion 12 is in a relaxed, expanded condition. Therefore, the arming flange 22 of control rod 20 is spaced axially from body portion 12, and the retaining sleeve 24 is spaced proximally from the carpule 2, such that release button 54 of spring arm 52 is positioned rearwardly of and out of engagement with the hole 18. Moreover, the stem 26 is located rearwardly of the control rod 20, such that the tip 30 thereof is also spaced rearwardly of and out of contact with the piston 3 of carpule 2.

The operation of the dental syringe 1 is now described while referring to FIGS. 5-9 of the drawings. Referring first to FIG. 5, an axially directed force is manually applied by the dentist in the direction of the reference arrow 56 to the arming flange 22 of control rod 20, whereby to move the control rod, against the bias of compression spring 14, distally through the hollow body portion 12 of syringe 1. The flexible spring arm 52 of control rod 20 is, likewise, moved distally through body portion 12 and slightly bent therein until release button 54 pops through hole 18 to lock the control rod and thereby prevent any further displacement thereof relative to body portion 12. Accordingly, the compression spring 14 is held in a compressed state at the distal end of body portion 12. What is more, the retaining sleeve 24 of control rod 20 is also moved distally through body portion 12 and into the syringe cylinder 6 via the open proximal end thereof so as to surround and engage the proximal end of carpule 2 and thereby secure said carpule against movement relative to the cylinder.

As a preferred embodiment of the present invention, and referring concurrently to FIGS. 5 and 5', a ring-shaped elastomeric (e.g. rubber) liner 58 extends around the interior periphery of the retaining sleeve 24 of control rod 20. The liner 58 includes a series of evenly spaced, radially inward extending projections 60 which establish a tight friction fit against the carpule 2 when the retaining sleeve 24 is advanced through the body 12 of syringe 1 to surround and engage the proximal end of said carpule. In this manner, the projections 60 of liner 58 may be slightly compressed to permit retaining sleeve 24 to firmly grasp carpule 2 and thereby assure that a subsequent rearward relocation of the control rod 20 through body portion 12 will cause a corresponding rearward relocation of the carpule 2 through cylinder 6 in a manner to be described when referring hereinafter to FIG. 8.

Figure 6:
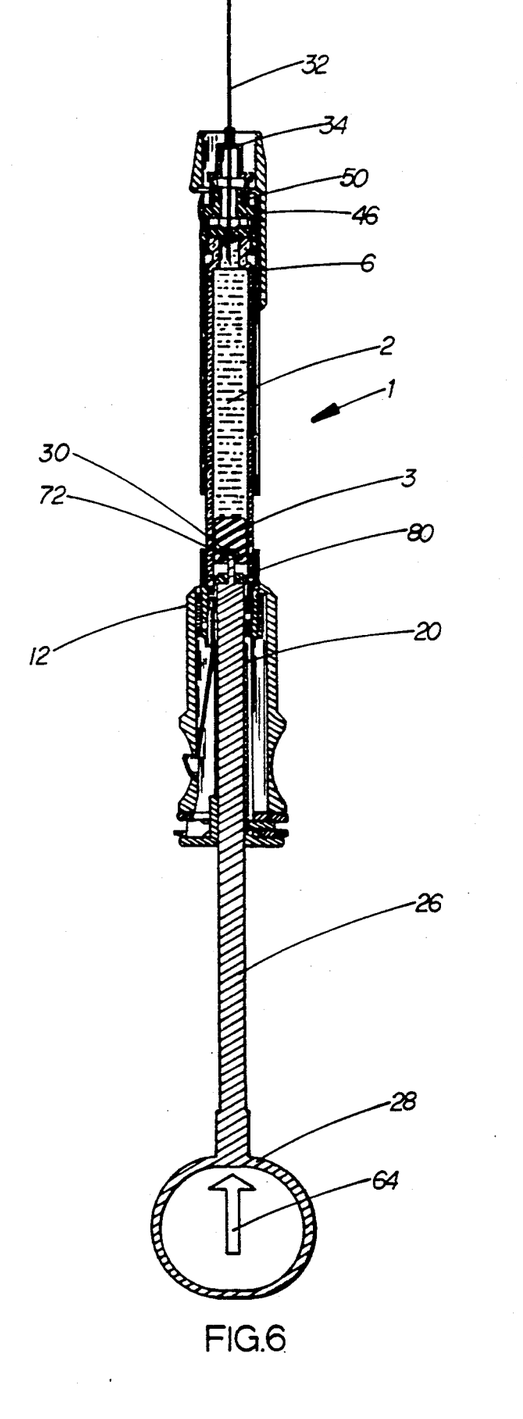
Figure 7:
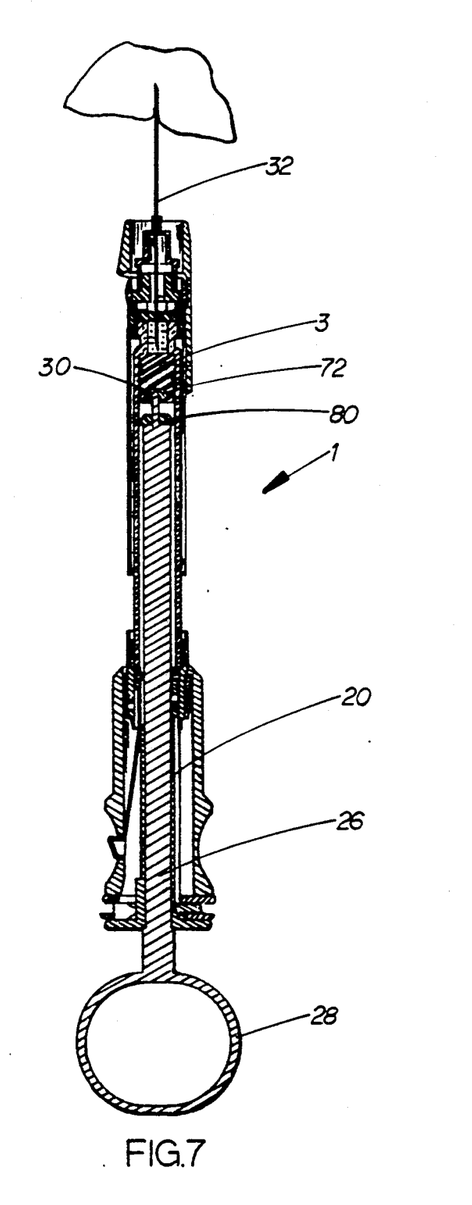

FIGS. 6 and 7 of the drawings illustrate the dental syringe in the injection state. More particularly, and referring to FIG. 6, with the control rod 20 advanced to and locked at a relatively distal position and the carpule 2 secured within the syringe cylinder 6 by retaining sleeve 24, the dentist applies an axial force in the direction of the reference arrow 64 to the thumb ring 28 of stem 26 to advance stem 26 distally through the hollow control rod 20 until the tip 30 penetrates the piston 3 of carpule 2 at the proximal end of cylinder 6. The conically-shaped tapered surface of tip 30 is inserted into frangible insert 72 such that radial gap 76 permits temporary dilation of insert ring 74. Once the conically-shaped tapered portion of the tip 30 is positioned distally of insert ring 74, reduced-diameter stem 27 extends through the insert ring which has returned to its initial, normal diameter, the radial gap in a relatively closed condition. Accordingly, a plunger is formed comprising stem 26, reduced-diameter stem 27, through ring 28 and to piston 3. Next, a conventional double-ended hypodermic needle 32, which is affixed to and supported by a conventional screw threaded hub 34, is interfaced with carpule 2 via the open distal end of cylinder 6. More particularly, the screw threaded hub 34 is mated to the screw threaded bore 50 of needle carrier 46 at the distal end of sleeve 4, such that the inwardly projecting end of cannula 32 penetrates the carpule to communicate the fluid contents thereof, and the outwardly projecting end of cannula 32 extends outside the cylinder 6 for administering an injection of said contents.

In FIG. 7, an injection is administered by syringe 1 in a medically accepted fashion. That is to say, the dentist first locates the outwardly projecting end of needle cannula 32 at a targeted tissue area of the patient. The dentist then resumes the application of the axial force to the thumb ring 28, whereby to continue the distal displacement of stem 26 through hollow control rod 20 for correspondingly driving the piston 3 through the carpule 2. The distal relocation of plunger 3 through the carpule 2 expulses a suitable volume of fluid medication to the patient via the needle cannula 32.

Figure 8:
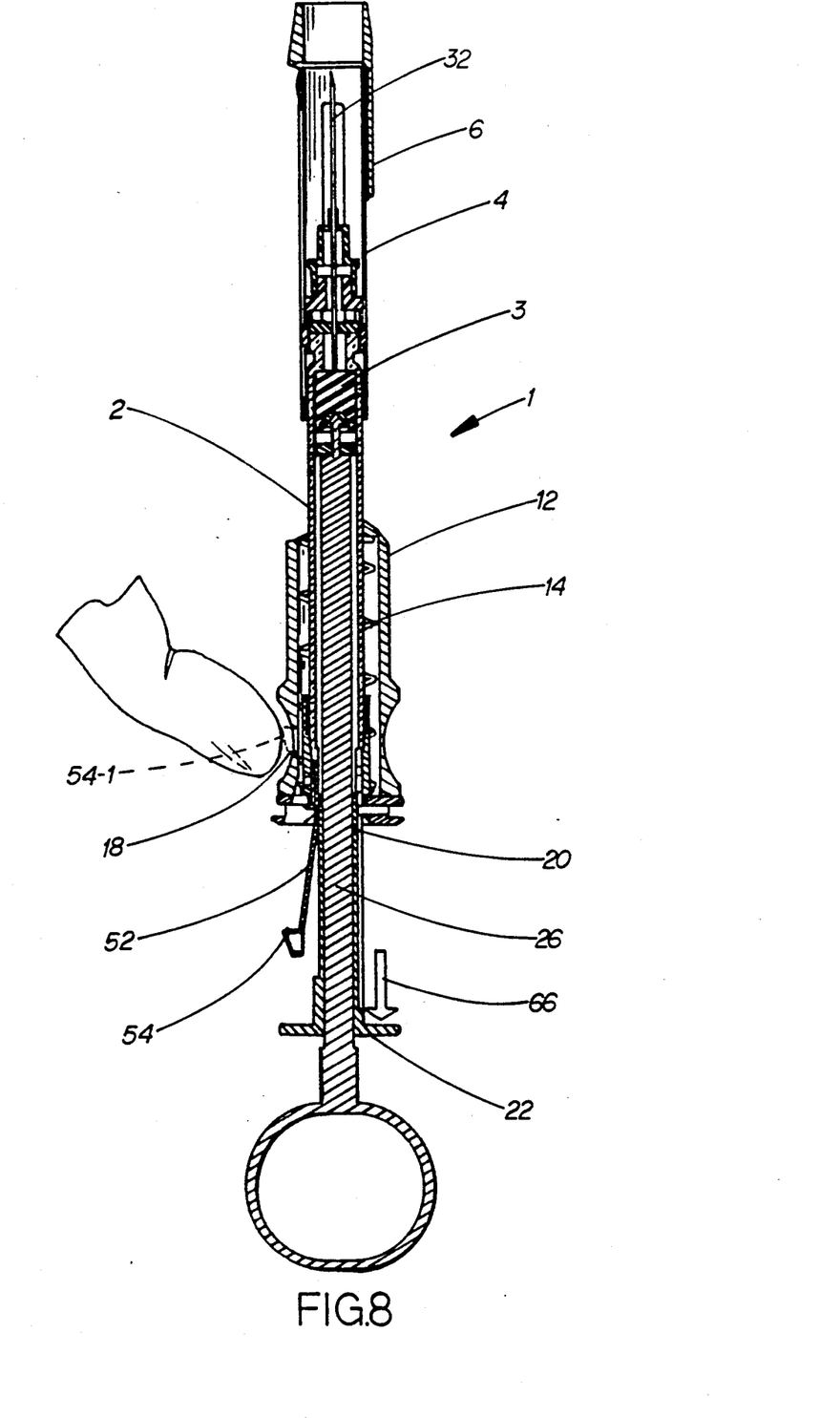
FIG. 8 is a cross-section of the dental syringe which illustrates an optional step of temporarily retracting the needle cannula into the syringe cylinder if an injection is to be administered in step-wise increments.

FIGS. 8 and 9 show the dental syringe in the post-injection state after an injection has been either partially (as seen in FIG. 8) or fully (as seen in FIG. 9) administered and the needle cannula has been removed from the patient's tissue. In FIG. 8, the needle cannula 32 is shown temporarily retracted within the syringe cylinder 6 to avoid an accidental needle stick prior to a resumption and completion of the injection. By way of example, it may be desirable to retract cannula 32 temporarily if the dentist wishes to momentarily lay the syringe in a dental tray and thereby administer the injection incrementally in two or more successive steps. In this case, the dentist depresses the release button shown in phantom and designated 54-1 against the bias of spring arm 52 to move the button inwardly of its hole 18 and thereby bend spring arm 52 in a radially inward direction. The depression of release button 52 through hole 18 unlocks the control rod 20 from its distally advanced position relative to the body portion 12 of syringe 1. The compression spring 14 is now free to return to its normal, expanded state, such that the stored potential energy within spring 14 will automatically and simultaneously drive control rod 20 and stem 26 in a proximal direction as indicated by the reference arrow 66 through body portion 12. The proximal movement of control rod 20 and stem 26 correspondingly causes the carpule 2 to be relocated proximally through cylinder 6 for receipt within body portion 12 via the open proximal end of the cylinder, whereby cannula 32 is safely retracted into the cylinder 6.

When the dentist later wishes to complete the injection, he once again applies an axial force to the arming flange 22 of control rod 20 to advance the control rod 20 and stem 26 distally through body portion 12 to return carpule 2 and cannula 32 to the injection state of FIG. 7. The piston 3 is then driven through the carpule 2 by means of stem 26 to expulse all (or another portion) of the remaining fluid medication. Of course, if all of the fluid were to be initially expulsed from carpule 2 during a single, continuous step, such that the temporary retraction of cannula 32 into cylinder 6 would not be needed, then the post-injection steps described with reference to FIG. 8 may be avoided.

In FIG. 9, the injection has now been completed so that the needle cannula 32 can be safely and permanently retracted into the sleeve 4. More particularly, the dentist uses his thumb and forefinger to grasp the proximal end of carpule 2 by way of the opposing opening 8 and window 10 through the cylinder 6 to thereby prevent the relocation of the carpule relative to the cylinder. Next, the dentist depresses the release button 54, moving the button inwardly and against the bias of spring arm 52 through the hole 18 to unlock the control rod 20 from its distally advanced position and permit compression spring 14 to return to the expanded state in the manner described while referring to FIG. 8.

Figure 13:
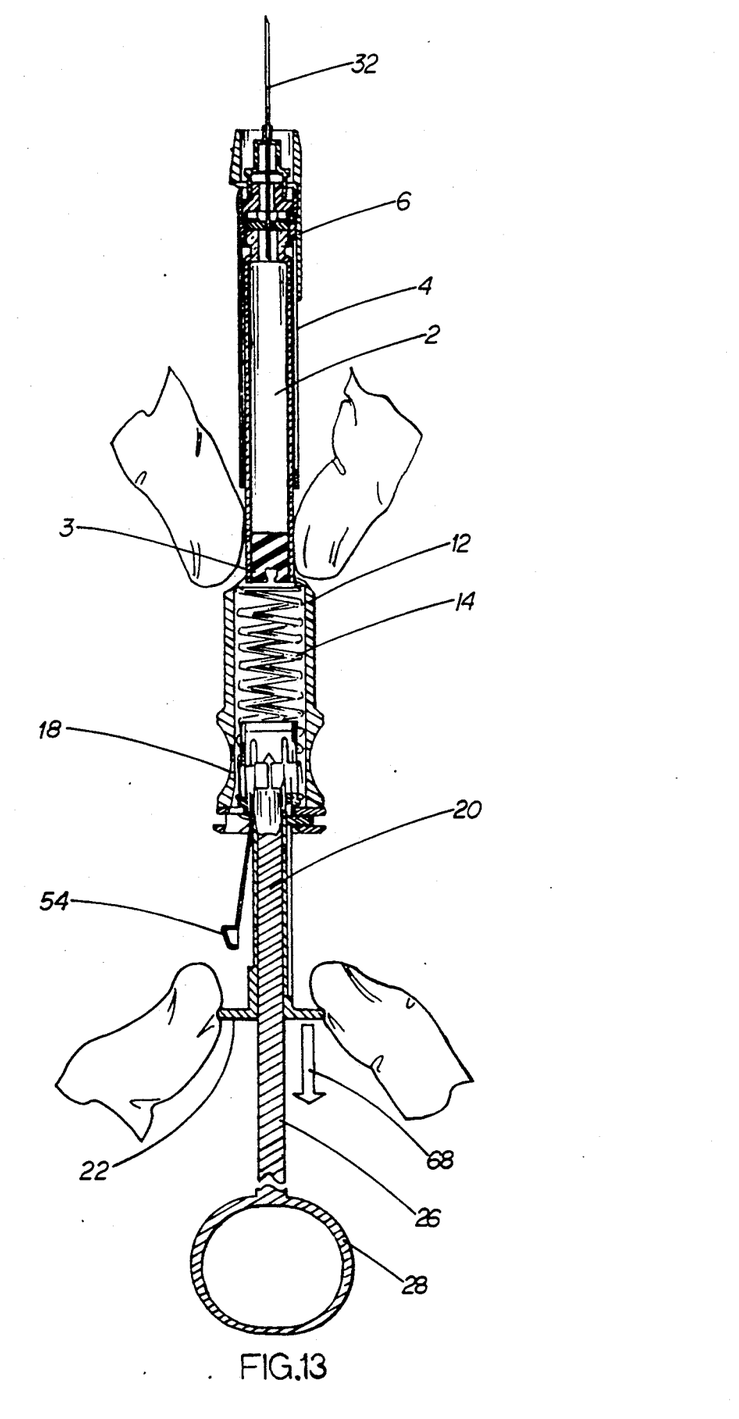
FIGS. 13-16 illustrate the retraction and anchoring of the needle cannula within the carpule sleeve to form a compact package suitable for handling and disposal in which the cannula is rendered irretrievable and nonreusable.

Referring now to FIG. 13, while maintaining a firm grasp on carpule 2 with one hand, the dentist uses his opposite hand to grasp and pull the arming flange 22 of control rod 20 in a rearward direction as indicated by the reference arrow 68. Pulling the arming flange 22 in a rearward direction correspondingly causes the control rod 20 and the retaining sleeve 24 thereof to be relocated proximally through the hollow body portion 12 of syringe 1. Therefore, the retaining sleeve 24 which previously surrounded and engaged the proximal end of the carpule 2 is now disengaged from said carpule to permit the carpule to be displaced relative to the syringe cylinder 6. The proximal relocation of the control rod 20 also displaces stem 26, whereby to detach the piston head 30 from piston 3. Flat proximal surface 29 of piston head 30 cooperates with frangible ears 78 for joint movement of control rod 20, sliding collar 80, and piston 3. With sufficient axial force exerted in the proximal direction, flat surface 29 breaks frangible ears 78, disengaging piston head 30 and frangible insert 72. The stem 26 may then be withdrawn from the carpule 2 by means of pulling the finger ring 28 in a rearward position.

Figure 14:
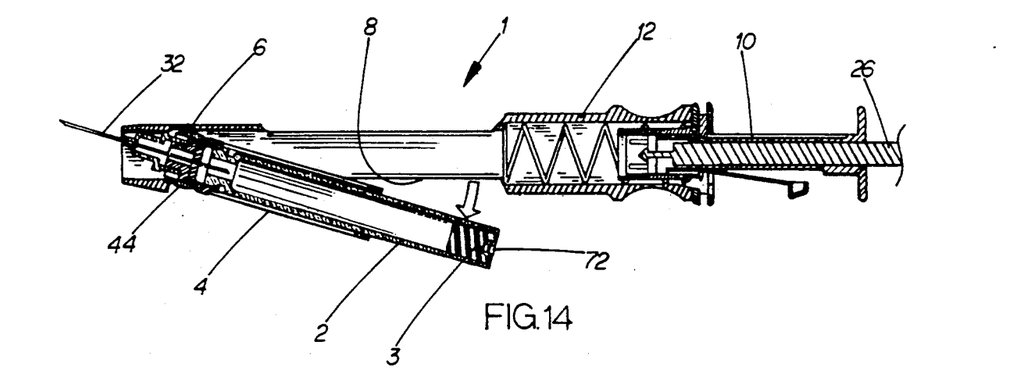
Figure 15:
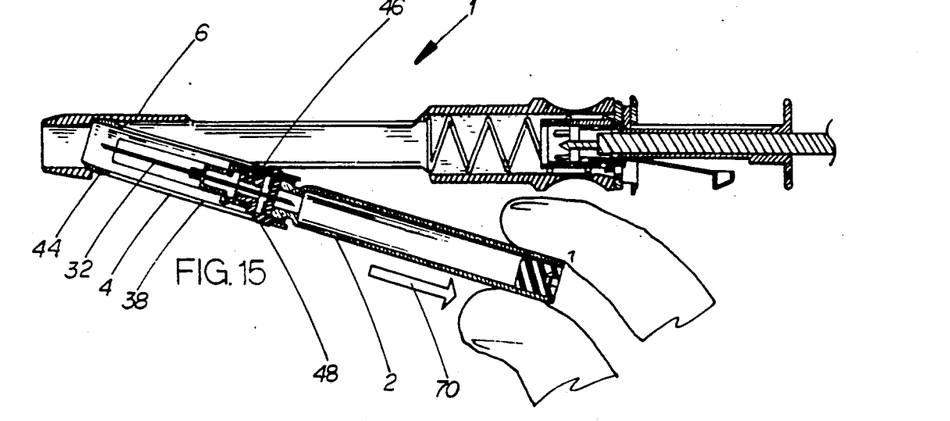
Figure 16:
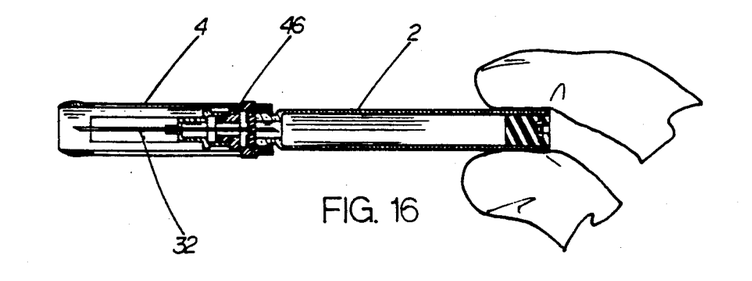

FIGS. 14–16 of the drawings illustrate the removal of the combination carpule 2 and sleeve 4 from the syringe cylinder 6 and the retraction of the needle cannula 32 into the sleeve. In FIG. 14, after the control rod 20 and stem 26 have been relocated proximally through the hollow body portion 12 of syringe 1, whereby carpule 2 can be displaced relative to the cylinder, the syringe 1 is turned so that the opening 8 through cylinder 6 faces downwardly. The combination carpule 2 and sleeve 4 are pivotally supported within cylinder 6 at the enlarged head 44 of sleeve 4 so as to rotate, under the influence of gravity, downwardly and outwardly from the cylinder via the opening 8 therethrough.

In FIG. 15, with the sleeve 4 still pivotally supported within cylinder 6 at the enlarged head 44 of the sleeve, the dentist grasps the carpule 2 and applies a proximal pulling force thereto in the direction indicated by the reference arrow 70. Accordingly, the carpule 2 and needle carrier 46 attached thereto slide proximally through sleeve 4, such that the latches 48 of carrier 46 ride through respective longitudinally extending tracks 38 in sleeve 4 until each latch 48 is seated in the space between a stop and a locking detent, designated 40 and 42 and best shown in FIG. 3, to prevent any further displacement of needle carrier 46. The needle carrier 46 is thereby anchored at the proximal end of sleeve 4 with the needle cannula retracted completely within and surrounded by the sleeve.

In FIG. 16, the dentist continues to apply a proximal pulling force to carpule 2 until the sleeve is separated from its pivotal attachment to the syringe cylinder 6. Accordingly, a compact disposal package is now available consisting of the empty carpule 2 pulled rearwardly through and locked by means of anchoring the needle carrier 46 within the sleeve 4. What is more, the needle carpule 32 is irretrievably located within sleeve 4 so as to be rendered inaccessible and non-reusable. Therefore, the disposal package may be safely handled and discarded while avoiding the possibility of an accidental needle stick and the threat of spreading a contagious, and conceivably life-threatening, disease. The dental syringe 1 of the present invention is then ready for sterilization and reuse with a fresh medication filled carpule, sleeve, and needle cannula in the manner that has been described above.

It will be apparent that while a preferred embodiment of the invention has been shown and described, various modifications and changes may be made without departing from the true spirit and scope of the invention. For example, although the syringe 1 has been described as having particular application as a dental syringe, it is to be understood that this is not to be regarded as a limitation of the claimed invention. That is, the syringe 1 is also adapted for any other use where a fluid is to be injected from a prefilled carpule.

Having thus set forth a preferred embodiment of the present invention, what is claimed is:

1. A syringe assembly comprising:
a hollow body portion having an elongated opening;

a sleeve receivable in said hollow body portion through said opening, said sleeve having distal and proximal ends;

a carpule for holding a fluid injection including means for securing a needle carrier thereto and being slidably disposed within said sleeve from a first position disposed at the distal end of said sleeve to a second position disposed at the proximal end of said sleeve, said carpule having distal and proximal ends;

detent means for retaining said needle carrier at said second position at said proximal end of said sleeve;

a piston disposed at the proximal end of said carpule and movable through said carpule to the distal end of the carpule for expulsing the fluid injection through the distal end of said carpule when said carpule is in said first position, the piston having a proximal end;

a frangible insert carried by said piston at the proximal end of said piston;

a stem including a tip for engaging said frangible insert for joint movement of said tip and said frangible insert and for returning said piston from the distal end of the carpule to the proximal end of the carpule;

stop means for preventing withdrawal of said piston from said carpule upon retraction of said stem an amount sufficient to remove said sleeve and carpule through said opening when said carpule is in said first position; and release means disposed on said frangible insert and being breakable for disengaging said tip and said frangible insert when said stop means prevents withdrawal of said piston.

2. The syringe according to claim 1 wherein said frangible insert comprises a ring, the ring having an inner circumference, and wherein said release means comprises frangible ears formed integrally with the inner circumference of said ring and being breakable upon retraction of said piston head.

3. The syringe assembly according to claim 2 wherein said frangible insert has a proximal end, and said frangible ears are disposed at the proximal end of said frangible insert.

4. The syringe assembly according to claim 2 wherein said piston is an elastomeric piston, and said frangible insert is embedded in said elastomeric piston and spaced from the proximal end of said elastomeric piston.

5. The syringe assembly according to claim 2 wherein said ring includes a radial gap to allow dilation thereof such that said tip is insertable into said frangible insert.

6. The syringe assembly according to claim 5 wherein said tip includes a tapered end facing the distal said ring for dilating said ring and a flat proximal surface opposite said tapered end adjoining said actuator rod for engaging said frangible ears.

7. The syringe assembly according to claim 2 wherein said stop means comprises a sliding collar surrounding said stem and wherein said body portion includes a shoulder, said sliding collar being movable into abutment with said shoulder such that the return of said piston to said proximal end of said carpule abuts said sliding collar and further retraction of said tip breaks said frangible ears.

8. The syringe assembly according to claim 1 wherein said piston is an elastomeric piston.

9. A carpule, for use in a syringe of the type having a stem comprising:

a fluid filled elongated body having proximal and distal ends;

a piston disposed at the proximal end of said elongated body;

a frangible insert carried by said piston at a proximal end thereof adapted to be engaged by the stem for joint movement of said piston and the stem from the proximal end of said elongated body to the distal end thereof so as to expulse fluid and for returning said piston to said proximal end of said elongated body; and release means disposed on said frangible insert and being breakable for disengaging said frangible insert from the stem upon retraction of said piston to said proximal end so as to prevent return of said piston upon further movement of said piston to said distal end.

10. The carpule according to claim 9 wherein said frangible insert comprises a ring having frangible ears formed integrally with the inner circumference of said ring and being breakable upon retraction of said actuation means.

11. The carpule according to claim 10 wherein said ring includes a radial gap to allow dilation of said ring such that the actuator is insertable into said frangible insert.

12. A syringe assembly comprising:

a hollow body portion having an elongated opening;

a sleeve receivable in said hollow body through said opening, said sleeve being of sufficient length to shield a needle therein, said sleeve having distal and proximal ends;

a carpule for holding a fluid injection including means for securing a needle carrier thereto and being slidably disposed within said sleeve from a first position disposed at the distal end of said sleeve such that the needle is adapted to project from said sleeve to a second position disposed at the proximal end of said sleeve, said carpule being slidable within said sleeve a sufficient amount to shield the needle within said sleeve, said carpule having distal and proximal ends;

detent means for retaining said needle carrier at the proximal end of said sleeve;

an elastomeric piston disposed at the proximal end of said carpule and movable through said carpule to the distal end of the carpule for expulsing the fluid injection through the distal end of said carpule, the piston having a proximal end;

a frangible insert embedded in said elastomeric piston at the proximal end of said elastomeric piston and spaced from the proximal end of said elastomeric piston, said frangible insert comprising a ring having a radial gap and an inner circumference and including frangible ears formed integrally with the inner circumference of said ring;

a stem including a tip having a tapered distal end for dilating said ring in cooperation with said radial gap to thereby engage said frangible insert, the tip having a flat proximal surface opposite said tapered distal end for engaging said frangible ears for joint movement of said stem and said elastomeric piston to return said elastomeric piston from the distal end of the carpule to the proximal end of the carpule;

a shoulder formed in said body portion;

a sliding collar slidingly surrounding said stem and being movable into abutment with said shoulder such that upon the return of said elastomeric piston to said proximal end of said carpule, said elastomeric piston abuts said sliding collar thereby preventing withdrawal of said elastomeric piston from said carpule, and whereby upon return of said stem an amount sufficient to remove said sleeve and carpule through said opening, said frangible ears are breakable to thereby prevent further joint movement of said tip and said frangible insert;

said carpule being slidable from said first position at the distal end of said sleeve in which the needle is adapted to project from said sleeve to said second position at the proximal end of said sleeve such that the needle is completely retracted within said sleeve, the needle being rendered completely inaccessible when said carpule is in said second position.

13. A syringe assembly comprising:

an elongated actuator including an elongated housing, the housing having proximal and distal ends, a stem assembly reciprocably movably carried by the housing having a first end protruding from the proximal end of the housing and a second end disposed with the housing, the distal end of the housing including an axially oriented bore and an elongated, generally radially oriented opening;

a carpule assembly including an elongated, open-ended sleeve and a fluid medication filled carpule having a distal end disposed with the sleeve and a proximal end protruding from the sleeve, the carpule assembly being formed for positioning within the housing adjacent the distal end of the housing by moving the carpule assembly through the housing opening, and an elastomeric piston at the proximate end of the carpule sealingly engaging the carpule and axially movable through the carpule towards the distal end thereof;

releasable locking means defined by the stem assembly and the piston comprising an engaging tip forming the second end of the stem assembly, a retainer carried by the piston adapted to engage the tip so that reciprocable movements of the stem assembly result in corresponding reciprocable piston movements between the ends of the carpule, the retainer including frangible means which break and thereby disengage the tip from the retainer and the piston in response to the application of a predetermined force between the piston and the tip acting in the proximal direction; and means for preventing axial movements of the piston relative to the carpule in a proximal direction past a predetermined location;

whereby, after breakage of the retainer, the stem assembly is separated from the carpule assembly and the carpule assembly can be removed from the housing through the opening thereof.

14. A syringe assembly according to claim 13 wherein a distal end f the sleeve and the distal end of the housing include means defining a pivotal joint formed and positioned so that the carpule assembly can be pivotally moved about the joint through the housing opening the joint further preventing relative axial movements between the sleeve and the housing until an axial force of a predetermined magnitude acts between them.

15. A syringe assembly according to claim 14 wherein the carpule is axially movable within the sleeve from a first position at which the distal end of the carpule is relatively remote from the proximal end of the sleeve to a second position at which it is relatively adjacent the proximal end of the sleeve, and including means preventing movement of the carpule in the proximal direction past the second position, and wherein the pivotal joint is constructed so that the axial force that must be applied to it to effect relative axial movement between the sleeve and the housing is greater than the axial force that must be applied to the carpule to move it from the first position to the second position.

16. A syringe assembly according to claim 13 wherein the retainer comprises a ring retainer secured to a proximal end of the piston and constructed to encircle the tip to thereby lock the piston to the stem assembly, the ring including a radial gap and the tip including a generally tapered end facing in the distal direction so that the tapered end engages and expands the ring retainer when the tip moves relative to the piston in a distal direction to facilitate the connection of the head to the piston.

17. A syringe assembly according to claim 16 wherein said frangible means are disposed on said ring.

18. A syringe assembly according to claim 13 further comprising stop means at the proximal end of the carpule for preventing withdrawal of the piston.

19. A syringe assembly according to claim 18 wherein said stop means comprises a sliding collar surrounding said stem assembly and wherein said housing includes a shoulder, said sliding collar being movable into abutment with said shoulder such that the return of the piston to the proximal end of the carpule abuts said sliding collar and further retraction of said stem assembly breaks said frangible ears.

20. An improved plunger assembly, for use with a syringe-type barrel structure of the type having distal and proximal ends, comprising:

a stem including a tip having an engagement surface facing away from the distal end of the barrel structure;

a piston body including a frangible stem engaging portion, the piston body adapted to be engaged by the tip of the stem with the engagement surface of the tip engaging the frangible stem engaging portion of the piston body to permit the piston body to e moved to a position towards the proximal end of the barrel structure by the stem after being driven towards the distal end of the barrel structure to expulse fluid; and release means disposed on the frangible stem engaging portion for disengaging the frangible stem engaging portion from the tip when the piston body is at the proximal end so to thereafter prevent the return of the piston body from the distal end towards the proximal end of the barrel structure.

* * * * *